United States Patent [19]
Amigues et al.

[11] 4,390,431
[45] Jun. 28, 1983

[54] PROCESS FOR TREATING AQUEOUS STREAMS CONTAINING ALUMINUM

[75] Inventors: Pierre Amigues, La Muladiere; Yves Chauvin, Le Pecq; Dominique Commereuc, Meudon; Jean Gaillard, Lyons; Nhu H. Phung, Antony, all of France

[73] Assignee: Institut Francais du Petrole, Rueil-Malmaison, France

[21] Appl. No.: 261,818

[22] Filed: May 8, 1981

[30] Foreign Application Priority Data

May 8, 1980 [FR] France ............................. 80 10360

[51] Int. Cl.³ ............................................. C02F 1/52
[52] U.S. Cl. ................................. 210/724; 210/737; 210/912
[58] Field of Search ............... 210/702, 708, 723, 724, 210/737, 912, 726; 260/439 R, 448 A; 208/13

[56] References Cited

U.S. PATENT DOCUMENTS

| | | | |
|---|---|---|---|
| 3,904,498 | 9/1975 | Hesse et al. | 208/13 |
| 3,909,405 | 9/1975 | Aoyama | 210/724 |
| 4,018,867 | 4/1977 | Lee | 260/448 X |
| 4,052,301 | 10/1977 | Klein et al. | 210/737 |

*Primary Examiner*—Peter A. Hruskoci
*Attorney, Agent, or Firm*—Millen & White

[57] ABSTRACT

A process for treating an aqueous phase obtained by acidic or basic washing of a hydrocarbon phase comprising a soluble aluminum compound in solution, characterized in that it is neutralized at a pH of from 6 to 8.5, treated with an additive selected from the alkaline-earth metal oxides, hydroxides and carbonates, at a temperature ranging from 90° C. to the boiling point, the molar ratio of the additive to aluminum being from 1/10 to 10/1, and separated thereafter from the insoluble phase of precipitate.

8 Claims, No Drawings

4,390,431

PROCESS FOR TREATING AQUEOUS STREAMS CONTAINING ALUMINUM

BACKGROUND OF THE INVENTION

This invention relates to the treatment of aqueous streams obtained by washing hydrocarbons produced by processes using soluble aluminum compounds.

In the processes for converting unsaturated hydrocarbons, such as dimerization, oligomerization, polymerization or alkylation, operated with trialkylaluminums, alkyl aluminum halides or aluminum halides, in the optional presence of transition metals, it is necessary to remove the metal compounds before subsequent fractionation treatments, so as to avoid undesirable secondary reactions.

This removal of the metal compounds can be effected easily by treating the hydrocarbon either with an aqueous solution of an acid, such as sulfuric acid, or with an aqueous solution of a base, such as sodium or potassium hydroxide. In the first case, aluminum and the other metals are found in the aqueous phase as soluble salts, such as sulfates; in the second case, aluminum is found as aluminate in the aqueous phase and the other metals are normally present as hydroxides.

The invention relates to the treatment of these aqueous streams, in order to make their disposal consistent with the pollution regulations. These streams cannot be discharged as such; it is necessary to bring them to a substantially neutral pH of, for example, 6 to 8.5 and to remove metals therefrom, particularly aluminum, down to very low contents.

The neutralization of acidic or basic streams results in the precipitation of aluminum as alumina gel or as mixed hydroxides gel which does not decant easily.

The object of the present invention is precisely a process improving the decantation of these gels and making their separation from the aqueous phase easier, so that the latter contain no more than traces of heavy metal ions.

The addition of various solid or liquid additives to the gel resulting from the neutralization of the aqueous hydrocarbon wash stream does not result in a substantial improvement of the decantation when these additives are added at room temperature. Among these additives a number of oxides, hydroxides and carbonates may be mentioned, such as $CaO$, $Ca(OH)_2$, $CaCO_3$, $MgO$, $Mg(OH)_2$, $MgCO_3$, $BaO$, $Ba(OH)_2$, $BaCO_3$, $Fe_2O_3$, $Fe(OH)_2$, $Fe(OH)_3$, as well as complexant acids such as tartaric, oxalic, lactic, or citric acid.

SUMMARY OF THE INVENTION

It has unexpectedly been found that the additives comprising alkaline-earth metal oxides, hydroxides or carbonates, particularly those of Mg, Ca and Ba, have a considerably increased effect on decantation when used in a narrow temperature range of from 90° C. to the boiling temperature of the mixture, which is about 105° C. when operating under normal pressure.

DETAILED DISCUSSION

The proportion of the alkaline-earth metal additive to be used is expressed with respect to the aluminum content of the aqueous hydrocarbon wash stream. The molar ratio of the additive to aluminum can vary from 1/10 to 10/1, preferably from 1/5 to 5/1.

The contact time of the additive with the aqueous stream containing the gel at a temperature of from 90° C. to the boiling point can vary from 1 minute to 5 hours and preferably from 10 minutes to 2 hours.

In a first embodiment of the invention, the neutralization of the aqueous wash stream followed with decantation can be effected continuously at rates in direct relation with the hydrocarbon production. In a second embodiment, the stream can be stored, and the neutralization and the decantation are effected periodically in batch.

The following examples illustrate the invention but do not limit its scope.

EXAMPLES 1 TO 5

523.3 g of an aqueous solution representing a purge stream from the destruction with NaOH of an olefin dimerization catalyst comprising nickel 2-ethyl hexanoate and dichloroethylaluminum in Al/Ni molar ratio of 15/1 are introduced into a 1 liter glass vessel. The composition of the solution is:

$NaOH = 14.59\%$ by weight
$NaCl = 2.64$
$AlO_2Na = 1.91$
$Ni(OH)_2 = 0.16$
$H_2O = 80.70$ This solution is carefully neutralized by adding 63.8 cc of 96% b.w. sulfuric acid, thus 116.7 g, which brings the pH to 8.5. The neutralized solution is then fractionated to 5 equal parts of 128 g each. A variable amount of powdered CaO is added to each fraction, except one, as indicated in Table 1, and the stirred contents are boiled for 1 hour. The contents are poured into a graduated test-tube to determine the decantation rate. The latter is estimated by the ratio, expressed as % and determined 30 minutes after the end of stirring, of the volume of the clear solution above the precipitate to the total volume of the suspension after neutralization. The aluminum, nickel and calcium contents of the decanted supernatant solution are determined by titration. The results are given in Table 1.

Example No. 1, in which no calcium oxide is present, is given by way of comparison; it shows that no decantation occurs in the absence of additive.

EXAMPLES 6 TO 13

120 g of a purge stream of the following composition:
$NaOH = 15.15\%$ by weight
$NaCl = 1.18$
$AlO_2Na = 2.17$
$Ni(OH)_2 = 0.26$
$H_2O = 81.24$ are introduced into a 250 ml glass vessel. This solution is carefully neutralized with 40 ml of concentrated aqueous hydrochloric acid (d=1.19), thus bringing the pH to 8.5. Variable amounts of powdered calcium oxide (CaO) are added and the stirred contents are boiled for variable times, as indicated in Table 2. This table gives in each case the decantation rate, expressed as in examples 1 to 5. The sodium, chlorine, aluminum and calcium contents of the decanted supernatant solution are given in the most favorable cases.

TABLE 1

| EXAMPLE No. | CaO added (mg) | Ca/Al (mole) | DECANTATION (%) in 30 mn. | ANALYSIS OF THE SOLUTION | | |
|---|---|---|---|---|---|---|
| | | | | Al (mg/l) | Ni (mg/l) | Ca (mg/l) |
| 1 | 0 | 0 | 0 | — | — | — |
| 2 | 170 | 0.125 | 63.3 | 20 | 0.2 | 380 |
| 3 | 340 | 0.250 | 84.6 | 50 | 0.3 | 510 |
| 4 | 680 | 0.500 | 11.6 | 60 | 0.4 | 590 |
| 5 | 1000 | 0.735 | 6.4 | 35 | 1.0 | 630 |

EXAMPLES 14 TO 16

These examples illustrate the importance of the contact temperature for the waste stream and the additive. The operating conditions and the purge stream are the same as in examples 6 to 13. 3.78 g of powdered CaO are added after neutralization in each experiment, corresponding to a Ca/Al molar ratio of 2/1, and the contact is maintained for 30 minutes at a temperature indicated in Table 3. The decantation rate is expressed as in examples 1 to 5.

EXAMPLE 17

The examples 6 to 13 are repeated with the same purge stream. After neutralization, powdered magnesium oxide is added in an amount of 2.70 g corresponding to a molar ratio Mg/Al, of 2/1, and the stirred contents are boiled for 1 hour. The decantation rate after 30 minutes is 75%.

EXAMPLE 18

The examples 6 to 13 are repeated with the same purge stream. After neutralization barium hydroxide is added in an amount of 11.56 g corresponding to a Ba/Al molar ratio of 2/1, and the stirred contents are boiled for 1 hour. The decantation rate is 55% after 30 minutes.

EXAMPLE 19

The examples 6 to 13 are repeated with the same purge stream. After neutralization calcium carbonate is added in an amount of 6.76 g corresponding to a Ca/Al molar ratio of 2/1, and the stirred contents are boiled for 1 hour. The decantation rate after 30 minutes is 65%.

TABLE 2

| EXAMPLE No. | CaO added (mg) | Ca/Al (mole) | BOILING time (min) | DECANTATION (%) in 30 min. | ANALYSIS OF THE SOLUTION | | | |
|---|---|---|---|---|---|---|---|---|
| | | | | | Na (g/l) | Cl (% b.w.) | Al (% b.w.) | Ca (% b.w.) |
| 6 | 3780 | 2 | 10 | 47.0 | — | — | — | — |
| 7 | 1890 | 1 | 30 | 28.5 | — | — | — | — |
| 8 | 3780 | 2 | 30 | 85.0 | 105 | 13.13 | <0.01 | 0.002 |
| 9 | 945 | 0.5 | 60 | 8.2 | — | — | — | — |
| 10 | 1890 | 1 | 60 | 16.8 | — | — | — | — |
| 11 | 3780 | 2 | 60 | 90.0 | 105 | 13.80 | <0.01 | 0.01 |
| 12 | 1890 | 1 | 120 | 14.0 | — | — | — | — |
| 13 | 3780 | 2 | 120 | 87.5 | 125 | 15.30 | <0.01 | 0.01 |

TABLE 3

| EXAMPLE No. | CONTACT TEMPERATURE (°C.) | DECANTATION (%) in 30 min. |
|---|---|---|
| 14 | 25 | 6.0 |
| 15 | 80 | 23.0 |
| 16 | 100 | 82.5 |

What is claimed is:

1. A process for removing aluminum values from a basic aqueous phase containing a water-soluble aluminum compound in solution, said basic aqueous phase resulting from the destruction of at least one of a hydrocarbon dimerization or oligomerization catalyst comprising a hydrocarbon-soluble aluminum compound and nickel by basic washing of a hydrocarbon phase containing said catalyst with an aqueous sodium hydroxide or potassium hydroxide solution, said process comprising neutralizing said aqueous phase with acid to bring it to pH of from 6 to 8.5, treating the resultant neutralized aqueous phase with an additive, said additive being an alkaline earth metal oxide, hydroxide or carbonate or a mixture thereof, at a temperature of from 90° C. to the boiling point of said aqueous phase, the molar ratio of the additive to aluminum being from 1/10 to 10/1, for a time sufficient to form an insoluble phase of precipitate, and thereafter separating the resultant aqueous phase, from the insoluble phase of precipitate.

2. A process according to claim 1, wherein the soluble aluminum compound dissolved in the hydrocarbon phase is a trialkylaluminum, an alkylaluminum halide or an aluminum halide.

3. A process according to claim 1, wherein the additive is a solid magnesium, calcium or barium oxide, hydroxide or carbonate, in powdered form.

4. A process according to claim 3, wherein the additive is calcium oxide or hydroxide.

5. A process according to claim 1, wherein the treatment of the neutralized aqueous phase is effected at a temperature of from 90° to 105° C.

6. A process according to claim 1, wherein the period of treatment is from 10 minutes to 2 hours.

7. A process according to claim 1, wherein the separation of the aqueous phase from the insoluble phase of precipitate is effected by decantation.

8. A process according to claim 1, wherein the molar ratio of the additive to the aluminum is from 1/5 to 5/1.

* * * * *